(12) United States Patent
Erler

(10) Patent No.: US 8,173,952 B2
(45) Date of Patent: May 8, 2012

(54) ARRANGEMENT FOR PRODUCING ELECTROMAGNETIC RADIATION AND METHOD FOR OPERATING SAID ARRANGEMENT

(75) Inventor: Marco Erler, Oberkochen (DE)

(73) Assignee: Carl Zeiss Industrielle Messtechnik GmbH, Oberkochen (DE)

( * ) Notice: Subject to any disclaimer, the term of this patent is extended or adjusted under 35 U.S.C. 154(b) by 469 days.

(21) Appl. No.: 12/373,313

(22) PCT Filed: Jul. 11, 2007

(86) PCT No.: PCT/EP2007/006163
§ 371 (c)(1),
(2), (4) Date: Jan. 12, 2009

(87) PCT Pub. No.: WO2008/006569
PCT Pub. Date: Jan. 17, 2008

(65) Prior Publication Data
US 2009/0242744 A1    Oct. 1, 2009

(30) Foreign Application Priority Data
Jul. 11, 2006  (DE) .................... 10 2006 032 607 U

(51) Int. Cl.
*G01D 18/00* (2006.01)
*G03B 11/00* (2006.01)

(52) U.S. Cl. .................................. 250/252.1; 250/482.1
(58) Field of Classification Search ............... 250/252.1, 250/504 R, 482.1
See application file for complete search history.

(56) References Cited

U.S. PATENT DOCUMENTS

| | | | | |
|---|---|---|---|---|
| 3,885,415 | A | * | 5/1975 | Burns et al. ..................... 73/1.41 |
| 5,020,086 | A | * | 5/1991 | Peugeot ........................... 378/113 |
| 5,841,835 | A | | 11/1998 | Aufrichtig et al. |
| 2001/0050972 | A1 | | 12/2001 | Yamada et al. |
| 2003/0169849 | A1 | | 9/2003 | Smyth |

FOREIGN PATENT DOCUMENTS

| | | |
|---|---|---|
| EP | 0874536 A1 | 10/1998 |
| EP | 1346689 A2 | 9/2003 |

\* cited by examiner

*Primary Examiner* — David Porta
*Assistant Examiner* — Faye Boosalis
(74) *Attorney, Agent, or Firm* — Laurence A. Greenberg; Werner H. Stemer; Ralph E. Locher

(57) ABSTRACT

A method for operating an assembly configured to produce electromagnetic radiation, especially X-ray radiation or extreme ultraviolet radiation. Particles, especially electrons, are guided onto a target by way of an adjustable focusing device. The particles produce electromagnetic radiation in the target. At least one object, especially a calibration object, is penetrated by the electromagnetic radiation and a radiogram of the object is recorded. The radiogram or a plurality of radiograms is automatically evaluated and the focusing device is adjusted depending on the evaluation.

23 Claims, 9 Drawing Sheets

ARRANGEMENT FOR PRODUCING ELECTROMAGNETIC RADIATION AND METHOD FOR OPERATING SAID ARRANGEMENT

BACKGROUND OF THE INVENTION

Field of the Invention

The invention relates to an arrangement for producing electromagnetic radiation, in particular X-ray radiation or extreme ultraviolet radiation, and to a method for operating such an arrangement. In this description, X-ray radiation and extreme ultraviolet radiation are understood to mean electromagnetic radiation which arises as a result of acceleration (deceleration) of particles at a focal spot of a target. The spectral ranges of X-ray radiation and extreme ultraviolet radiation are not restricted by specific wavelengths or photon energies.

The invention also relates, in particular, to the field of examination of industrially and/or technically produced articles by means of electromagnetic radiation. By way of example, it is known to radiate X-ray radiation through a workpiece and to record an X-ray image, to repeat the process for different directions of incidence of the X-ray radiation and then to produce three-dimensional, reconstructed X-ray images of the workpiece by means of a computer. The reconstruction on the computer is referred to as computer tomography (CT).

In particular, a radiation producing device of the arrangement according to the invention can be a microfocus X-ray tube.

In microfocus X-ray tubes, in particular, the size of the focal spot at which impinging particles (usually particles of an electron beam) produce the X-ray radiation is not constant with respect to time. The focal spot generally increases in size as time progresses. In the case of CT, however, high powers of the tubes used for producing the X-rays or other short-wave electromagnetic beams are desirable. As a rule of thumb it holds true that the time for recording the radiographs can be halved if the radiation power of the tube is doubled. As the size of the focal spot increases, however, the spatial resolution in images that could be obtained with an ideally point-type X-ray source is impaired. The temporal change in the size of the focal spot is therefore to be prevented.

U.S. 2001/0050972 A1 describes an X-ray radiation generator that is able to automatically focus an energy beam, e.g. an electron beam. According to the description of the document, there is a close relationship between convergence conditions of an energy beam and the surface temperature of the target of the X-ray tube. Therefore, the document proposes measuring the temperature changes in real time and automatically controlling the current value of a focusing coil.

It appears to be open, however, how meaningful the temperature of the target are for the focusing of the particles (the latter are understood to be in particular electrons or quanta of an electromagnetic radiation). Although the inventor's findings confirm a dependence of the focusing on the temperature of an X-ray tube, the focusing can depend not only on the target temperature but also on other influencing factors, e.g. on how and how effectively the target is cooled.

The method described in U.S. 2001/0050972 A1 additionally presupposes that the optimum focal spot size or the optimum focusing was found in some other way at the beginning of the operation of the X-ray tube. The observation of the change in temperature of the target does not provide any information with regard to this.

Moreover, the optimum focusing can differ in different operating ranges and/or for different operating modes of the radiation producing device.

BRIEF SUMMARY OF THE INVENTION

Therefore, it is an object of the present invention to specify an arrangement for producing electromagnetic radiation and a method for operating such an arrangement which enables the focal spot size to be automatically adjusted under different operating conditions. In particular, the intention is to be able to adjust the spatial resolution in a radiograph that can be recorded using the electromagnetic radiation produced from an object, and preferably to regulate it to a predetermined value and/or to the maximum.

It is proposed to arrange at least one object, in particular at least one specific calibration object, in the beam path of the electromagnetic radiation produced, such that the electromagnetic radiation radiates through the object (or the objects). Furthermore, a radiograph of the object or objects is recorded. Optionally, further radiographs of the object or objects can be recorded. The radiograph or radiographs is or are automatically evaluated and a focusing device is adjusted in a manner dependent on the evaluation. The focusing device directs the particles onto a target of the radiation producing device, such that the electromagnetic radiation is produced by the particles in the target. In this way a self-contained action circuit arises which is preferably operated such that the focusing device is the actuating device of a closed-loop control circuit. In this case, for the spatial resolution to be obtained in the radiograph and/or for an image contrast of the radiograph, a value to which the spatial resolution actually obtained and/or the image contrast actually obtained is regulated can be predetermined. As an alternative or in addition, the maximum of the spatial resolution (that is to say the finest resolution) and/or the maximum of the image contrast can be predetermined or the maximum of the spatial resolution and/or of the image contrast can be determined automatically by varying the adjustment of the focusing device.

The spatial resolution (or resolving power) can be defined as the ability still to be able to reproduce predetermined extremely small structures. The resolving power of an image recording device can be specified by the modulation transfer function (MTF). In order to determine the resolution, image recordings of line patterns or other predefined structures can be concomitantly produced. Preferably, however, as will be described in greater detail on the basis of an exemplary embodiment, the resolution is determined only indirectly via the rate of change of image values (e.g. grey-scale values) in an evaluation direction.

In the case of digital radiographs, the minimum (tolerable) spatial resolution in the radiograph, corresponding to a specific focal spot size or radiance of the electromagnetic radiation, results from the pixel size of the image recording device and from the magnification of the object. This minimum (worst) resolution, or a better resolution can be predetermined, for example. In this case, it is preferably also taken into account that the target can be damaged in the case of an excessively small focal spot size. Therefore, a range exists for the resolution, which range can be limited downward (worst tolerable resolution) and upward (best, finest resolution without damage). If at least the worst resolution is obtained, the radiation source does not have a restrictive effect for the resolution and thus for the information that is detected in a digital image. The range of the best resolution is generally given by the loading limit of the target, that is to say of the power of the particles incident on the target. These considerations hold true for a recording time period of fixed length. If the recording time period is lengthened, for the same illumination of the image recording device the target power can be reduced proportionally, with the consequence that a higher resolution can be obtained if the resolution limit given by the pixel size has not yet been reached. Conversely, the recording time period can be shortened by means of a higher power. Since, with the present invention, the maximum (best) resolution can be adjusted anew and/or maintained over a time period, the recording time period can be shortened as far as possible.

In particular, the predetermined value and/or the maximum is checked (preferably multiply repeatedly) during the operation of the arrangement and the focusing device is readjusted as necessary, such that the desired value is achieved again. For this purpose, the specific calibration object can be repeatedly introduced into the beam path of the electromagnetic radiation, in which case, particularly when the maximum are intended to be adjusted or found, it is possible for the actual measurement object that is the subject of the radiation examination to remain in the beam path.

The invention has the advantage that the adjustment of the focusing device is performed on the basis of information that is the result of all the influencing factors. In other words, account is taken not only of the temperature of the target but also, in particular, of the dependence of the focal spot on e.g. an accelerating voltage and on the particle current of the X-ray tube. Moreover, an adjustment of the focusing device can even be performed in a direction-specific manner by evaluation of the radiograph in different directions (e.g. both in the X direction and in the Y direction of a system of Cartesian coordinates of the image), e.g. in order to compensate for an astigmatism. In this case, the focusing device can have at least two adjustable parameters, e.g. the coil currents of two coils, wherein each of the coils influences the focal spot size selectively or predominantly only in one of two different directions along the surface of the target.

The invention can also solve yet another problem in the operation of radiation producing devices, in particular X-ray tubes: the focal spot in the target is a demagnified and, under certain circumstances, slightly distorted image of the emission spot at the heating filament. The heating filament changes its cross section and thus its electrical resistance over the course of its lifetime. Therefore, the current through the heating filament should be readjusted at best continuously, but at least repeatedly. If correct readjustment is not effected over the entire power range of the heating filament and thus of the particle beam, two possibilities arise.

Firstly, the heating filament current can be too high, with the result that although the emission spot remains optimally small, the lifetime of the heating filament decreases unnecessarily.

Secondly, the heating filament current can be too small. This results in a low current density of the electron-emitting area, with the consequence that a grating diaphragm (e.g. configured as a Wehnelt cylinder and) acting as an electrostatic lens between heating filament and anode uses the electrons from a larger emission area. The emission current that is effective for the electrons incident on the target can therefore be regulated or adjusted via the grating diaphragm. The current density of the electrons which form the emission spot (or issue from the latter) is then non-uniform owing to the excessively small heating filament current (relative to the location). Moreover, the emission spot cannot be reliably determined and controlled. The form of the focal spot varies in this case from heating filament to heating filament and over the course of the life of a heating filament. By contrast, if the heating filament current is at an optimum, the variation of the focal spot form is very small.

This non-uniform and also larger emission spot causes a non-uniform and magnified focal spot, which can in turn lead to a blowing of structures in the recorded image (that is to say to structures less sharp in the image than in the object). In the worst case, a double image can be registered at individual or grating structures. According to the invention, this can be identified with the aid of one or more calibration objects and be automatically corrected by evaluation of at least one radiograph and adjustment of the heating filament current. In this case, the calibration objects have, in particular, structures (as will be described later, e.g. structures with rays of a Siemens star) which have a continuously varying structure width (e.g. width and spacing of the rays change continuously from radially at the inner end to radially outward). It can therefore be identified that double images are produced with a specific structure width.

Since the heating filament current in conjunction with the grating diaphragm (or some other device) leads to a first, anodal focusing (prefocusing) that makes its contribution to the adjustment of the optimum focal spot size at the target:

an adjusting device for adjusting the heating filament current (or for adjusting some other device for emitting the particles that are radiated onto the target) and/or an adjusting device for adjusting the focusing effect of the grating diaphragm, the aperture diaphragm or some other electrostatic lens are also understood as a focusing device or part(s) of a focusing device. However, the invention is not restricted to a focusing device with such an adjusting device, nor to X-ray tubes with a grating diaphragm. Rather, specific configurations of the invention involve merely adjusting e.g. a magnetic field (or electric field) which focuses the already existing particle beam.

The focusing has the task of demagnifying the primary focal spot on the heating filament through to the target. In the case described above, this is achieved firstly by the electrostatic focusing at the cathode itself. The grating diaphragm or aperture diaphragm, embodied e.g. as a Wehnelt cylinder, has the effect that the diaphragm, which is at a negative potential, repels the particles (electrons) and concentrates them in this way, with the consequence of a first constriction—lying in the anode plane—of the particle beam ("crossover"). After this pre-demagnification or prefocusing, e.g. a conventional magnetic focusing is effected behind the anode in the region free of an electric field.

Moreover, in one development of the invention, further variables that influence the radiograph can be taken into account, such as e.g. the focus-object distance (FOD), the focus-detector distance (FDD) and the type of target. FOD and FDD determine the geometrical relations. Using the geometrical relations and using the information about the size of a pixel in the radiograph, the resolution or unsharpness (as results from the spatial resolution) produced by the radiation source can be predetermined and/or adapted to the size of a voxel determined by the geometrical relations and the size of the pixel, after a CT reconstruction. The focusing device is correspondingly adjusted for the adaptation. In order to be able to perform the adjustment, an assigned resolution can be determined by evaluation of the radiograph or radiographs and from this, in particular taking account of a predetermined relationship between the magnification and the edge length of a pixel, the voxel size assigned to the reconstructed image or reconstructed images can be calculated. If this size does not correspond to the predetermined value and/or to the minimum that can be achieved, the focusing device can be correspondingly adjusted.

Not only in the embodiment described in the preceding paragraph, in the adjustment of the focusing device further information could be taken into account in addition to the result of the evaluation of the image or images. By way of example, the accelerating voltage and the electron current of an X-ray tube and/or the instantaneous power of the particles impinging on the target can be taken into account. As an alternative or in addition, the properties of the target or of further parts of the radiation producing device, such as e.g. of a base to which the target is fixed and/or of a window through which the electromagnetic radiation passes, can also be taken into account. As an alternative or in addition to the desired values of the operating variables (e.g. particle current, accelerating voltage) of the radiation producing device, it is possible to use wholly or partly measured values of said variables. Further desired variables or measurement variables which can be taken into account in the adjustment are variables which define the state of other parts of the radiation producing device, of parts of the arrangement for recording the radiographs and the evaluation thereof, and/or of variables which describe the environment, such as, for example, one or more temperatures of the parts and/or of the environment. Dependencies between one or more of these variables among one another and/or on the state of the focusing device and/or on the focal spot size may have been established beforehand and be available and used for example in the form of a table or a plurality of tables for the adjustment of the focusing device.

A further aspect of the invention relates to a calibration object which can be used for the adjustment of the focusing device. The calibration object can be introduced into the beam path of the electromagnetic radiation, such that the latter radiates through said calibration object and a radiograph is recorded. The information required for the adjustment of the focusing device can be obtained by evaluation of said radiograph or a plurality of radiographs. The calibration object can be introduced into a predetermined position relative to the target into the beam path using a movable mount. The mount can be configured such that the calibration object is removed from the beam path or returned to the predetermined position in the beam path by actuation of the mount. By way of example, the calibration object is fixed to a part of the mount which can be brought to a position corresponding to the predetermined position by rotation and/or by a linear movement, wherein the part preferably latches and/or can be locked in this position.

It is thereby possible, during a measurement of a measurement object, to bring the calibration object repeatedly to the predetermined position and to use the resulting radiographs for the correction of the adjustment of the focusing device. In this case, the movable mount is preferably connected to the radiation producing device, such that the predetermined position can be attained reproducibly solely on account of this connection. It is also advantageous for the calibration object and/or the filters to be arranged in the beam path directly behind the exit cross section through which the radiation emerges from the radiation producing device. In this way it is possible to obtain a very large magnification of the calibration object in the radiograph or to ensure the filtering with a small filter size over the entire exit cross section.

In radiography it is customary to use at least on occasion filters through which the radiation passes, such that the spectrum of the radiation is altered. Preferably, the mount has one or more filters for filtering the radiation, such that optionally one or more filters and/or the calibration object can be introduced into the beam path of the electromagnetic radiation by actuation of the mount. The calibration object can consequently be considered like a specific filter which, however, does not, or does not exclusively, influence the spectrum of the radiation, but rather attenuates the intensity of the radiation in defined solid angle ranges.

Therefore, no, or only insignificantly more, additional space is required by the integration of the calibration object into the mount.

If the calibration object and a measurement object are simultaneously situated in the beam path of the electromagnetic radiation, the calibration object is preferably arranged nearer to the target than the measurement object. Preferably, the calibration object (for example as already described) is arranged or fixed on the radiation producing device, wherein the radiation producing device has the target.

Advantages of this arrangement are, as already mentioned, the magnification of structures of the calibration object with a high magnification factor, the simple handling of the calibration object and the exactly reproducible positioning of the calibration object in the beam path.

In particular, a calibration object is preferred which has structures formed by edges of a material or by edges and/or margins of a plurality of materials. Edges are understood to be, in particular, surfaces of the respective material which are preferably arranged such that they run in the direction of their edge height and in the direction of the optical axis of the electromagnetic radiation or parallel to the optical axis. In this case, the edges do not have to run exactly parallel or in the direction of the optical axis, particularly if they are arranged in the outer region of a radiation cone of the radiation.

In one embodiment of the method according to the invention, during the evaluation of the at least one radiograph, in the respective image along a line running transversely with respect to an edge profile produced by the edges, a change in image values, in particular in grey-scale values, is evaluated and the focusing device is adjusted depending on the change. The edge profile is understood to be an image structure produced by the respective edge in the radiograph. If an extinction of the radiation takes place in the material having the edge, the edge profile is a more or less sharply progressing transition between an image region which corresponds to a lower radiation intensity and an image region which corresponds to a higher radiation intensity. Therefore, e.g. the grey-scale value images customary for radiography involve a transition between regions having different grey-scale values. On the basis of the evaluation of the radiograph along the abovementioned line running transversely with respect to the edge profile, the sharpness or abruptness of the change in the image values can be established and used for the adjustment of the focusing device. By way of example, only the image value differences between adjacent pixels which lie on the line are evaluated. In this evaluation, high differences between adjacent pixels along the line can be overweighted in order to be able to establish the sharpness of the transition at the edge profile. By way of example, the square of the difference in image values between adjacent pixels is formed in each case and all the squares are summed. It is furthermore preferred for the line along which evaluation is effected to intersect a plurality of the edge profiles.

It is furthermore preferred to evaluate the change in the image values along two different lines running transversely with respect to one another in the respective image. In particular, the lines can run in the direction of the rows and/or columns of a detector matrix of the image recording device. In this way it is possible to establish that the image is sharper in one direction than in the other direction. This is preferably taken into account in the adjustment of the focusing device. For this purpose, the focusing device can have e.g. a second electromagnetic winding and/or an additional electron lens which focuses the electron beam only with regard to a direction transversely with respect to the propagation of the electron beam.

The calibration object is preferably suitable for adjusting the adjustment of the focusing device in different power ranges. Power is understood here to mean that power with which the particles are radiated onto the target, that is to say e.g. the electrical accelerating power for accelerating electrons of an electron beam directed onto the target.

In a concrete embodiment of such a calibration object, the structures have a first partial structure and a second partial structure, wherein distances between the edges and/or the margins are larger in the first partial structure than in the second partial structure of the calibration object. This does not rule out a situation where individual distances or the distance are or is smaller in a small part of the first partial structure than in a small partial region of the second partial structure. On average or predominantly, however, the distances in the first partial structure are larger.

The first partial structure can therefore be used at high powers, and the second partial structure can be used at small or lower powers.

Particular preference is given to a calibration object in which material regions forming the edges are shaped like the rays or segments of a Siemens star and are arranged relative to other rays, in which case, however, unlike in the Siemens star, it is not necessary for all the rays to be present with a constant angular distance with respect to one another. Rather, it is preferably the case that, from the point of view of the center, only a plurality of rays in each case extend radially outward in partial angular ranges around the center. Other angular ranges, by contrast, contain no rays or rays having a different angular width. The angular width is understood to mean the angular distance between the two outer edges of the ray.

In particular, the first and second partial structures can be realized in this way: rays having a smaller angular width are arranged in at least one angular range (second partial structure) and rays having a larger angular width are arranged in at least one angular range (first partial structure). In this case, the angular distance between the rays having the same angular width is preferably equal to the angular width in the respective angular range.

To put it more generally, and thus detached from the concrete exemplary embodiment described above, the edges and/or margins of the first partial structure and of the second partial structure extend in different solid angle ranges relative to a propagation space of the electromagnetic radiation, such that a radiograph of the first partial structure and of the second partial structure can be recorded simultaneously. In this case, the second partial structure is arranged nearer to the target than the first partial structure in the beam path of the electromagnetic radiation. It is thereby possible to obtain a magnification corresponding to the size of the distances in the radiograph. The two partial structures can preferably also differ with regard to their aspect ratio, which is defined as the ratio of the height to the distance, that is to say is defined here in particular as the ratio of the edge height to the distance between the edges and/or margins. The height is determined in a direction running approximately in the propagation direction of the radiation. In the embodiment with rays similar to the Siemens star, the aspect ratio is formed for example with the distance that exists in the radial direction in the center of the rays between the edges and/or margins.

Preferably, the structures are arranged such that the edges and/or margins extend transversely with respect to the propagation direction of the electromagnetic radiation and approximately in a direction which runs radially outward from the optical axis of the radiation. In the case of the rays of a Siemens star, the optical axis (defined by the straight connecting line from the focal spot to the center of the detector arrangement and/or through the central axis of the radiation cone) therefore pierces the calibration object preferably at the center of the rays.

One preferred embodiment of the calibration object has a carrier material which is transparent to the electromagnetic radiation and which has, in particular, a disc-shaped body having two parallel surfaces. If the carrier material is arranged in the beam path of the electromagnetic radiation, the radiation passes through the carrier material preferably approximately perpendicular to the surfaces of the disc. One preferred carrier material is glassy carbon, which is a highly technological material composed of pure carbon and combines vitreous and ceramic properties with properties of graphite.

The material regions forming the edges and/or margins are applied to the in particular disc-shaped carrier material e.g. by a galvanic method (that is to say by deposition in a corresponding bath). As an alternative, the material regions can be produced in particular using lithographic techniques such as are known from the production of microelectronic components. CVD (Chemical Vapor Deposition) or PVD (Physical vapor Deposition) processes can be performed in this case. One preferred material for forming the edges and margins is highly absorbent gold.

The above general description of the method according to the invention has variously also already discussed features of an arrangement according to the invention for producing electromagnetic radiation. The arrangement has, in particular, the following:
- an adjustable focusing device, which is configured for directing particles (in particular electrons) onto a target, such that the electromagnetic radiation is produced by the particles in the target (or by the deceleration of the particles in the target),
- an image recording device for recording radiographs of objects through which the electromagnetic radiation radiates (in particular from a calibration object),
- an evaluation device, which is connected to the image recording device and which is configured for automatically evaluating the radiograph or a plurality of radiographs, and
- an adjusting device, which is connected to the evaluation device and which is configured for adjusting the focusing device depending on a result of the evaluation in the evaluation device.

The calibration object already described above can be part of the arrangement. However, the invention also extends to a calibration object as an independent subject matter.

Exemplary embodiments of the invention will now be described with reference to the accompanying drawing. In the individual figures of the drawing:

DESCRIPTION OF THE INVENTION

Figure 1:
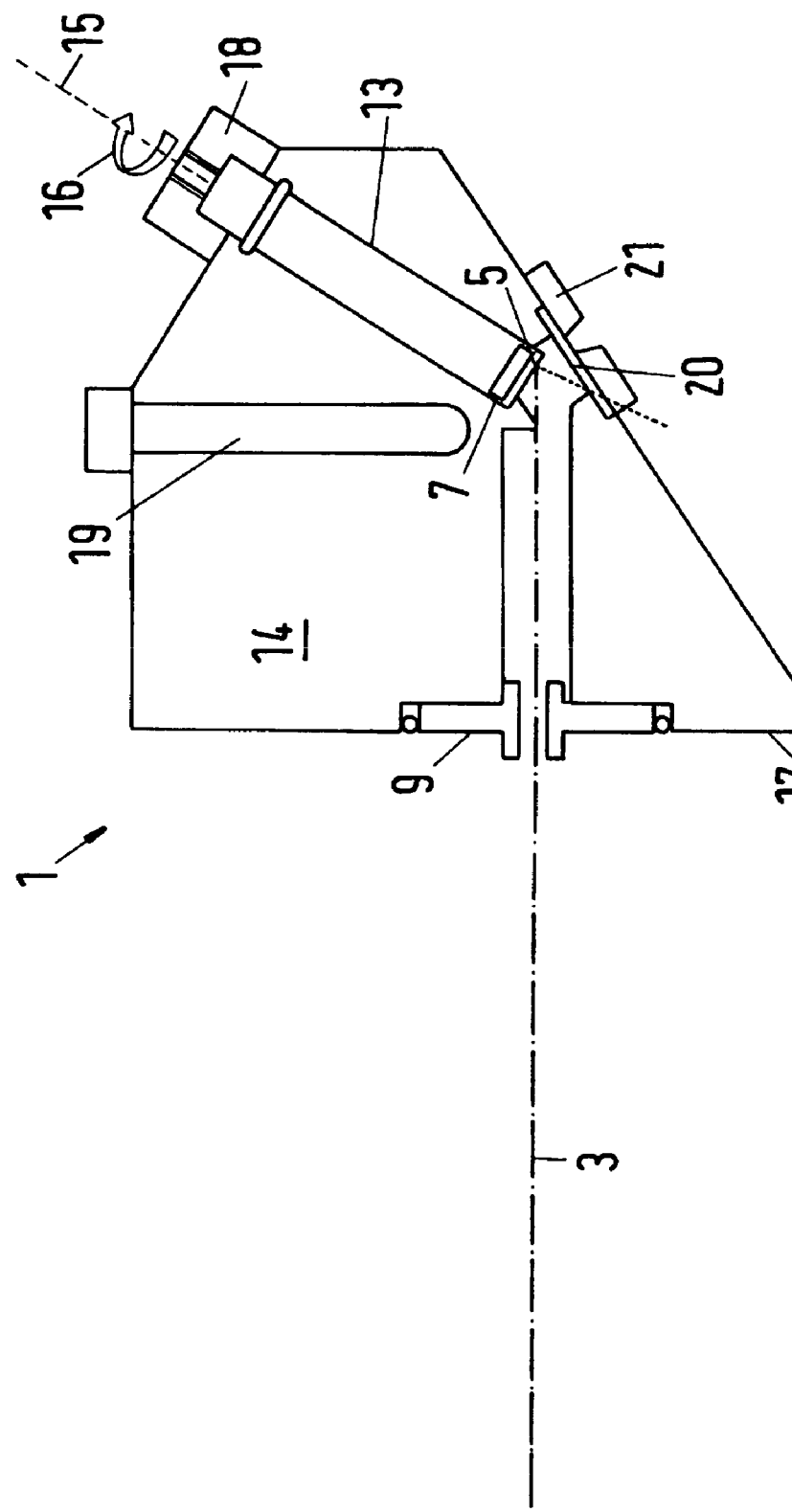
FIG. 1 shows an X-ray tube for producing X-ray radiation,
FIG. 2 schematically shows an arrangement for producing electromagnetic radiation with an adjustable focusing device,
FIG. 3 schematically shows a coil for focusing a particle beam onto a target.

FIG. 1 shows a schematic longitudinal section through a radiation producing device 1, which is an X-ray tube.

A dash-dotted line 3 represents the direction of incidence in which electrons enter into the radiation producing device 1 through an electron diaphragm 9 and impinge on a target 5 composed of tungsten foil.

Moreover, in addition to the electron diaphragm 9, a focusing device (not illustrated in this figure) for focusing the electrons onto a focal spot of the target 5 is provided within the evacuated interior 14 of the radiation producing device 1. Adjustable focusing devices are known from the prior art, e.g. from U.S. 2001/0050972 A1, and are therefore not described in greater detail here. The invention can be implemented with such a focusing device.

The target 5 is carried by a base 7 composed e.g. of diamond. On the opposite side of the base 7 from the point of view of the target 5, the base 7 is carried by a solid rod 13 composed of copper. The rod 13 and therefore also the base 7 and the target 5 can be manually rotated about a central longitudinal axis 15 of the rod 13, as is also indicated by an arrow 16, and a knurled mechanism 18 is provided at the opposite end of the rod 13 from the point of view of the target 5, said mechanism enabling the rod 13 to be rotated about the longitudinal axis 15.

Moreover, a cooling device 19 for indirectly cooling the target 5 and the base 7 is provided. Indirect cooling is understood to mean that neither the target nor the base is directly in contact with the cooling device or a coolant of the cooling device. During the operation of the arrangement 1, the cooling device 19 takes up heat through thermal radiation and via material bridges (not illustrated in specific detail) between the rod 13 and the cooling device 19 and transports said heat away.

The X-ray radiation produced by the target 5 is absorbed apart from the radiation which passes through a window 20 (for example composed of beryllium or diamond) that is transmissive to X-ray radiation. The absorption is effected by the tube head itself or by a shield surrounding it. In the direction of the measurement object and image recording device, the radiation emitted by the radiation source on all sides is collimated to a useful beam cone by a collimator 21 arranged before or after the window 20 in the beam path.

Figure 2:
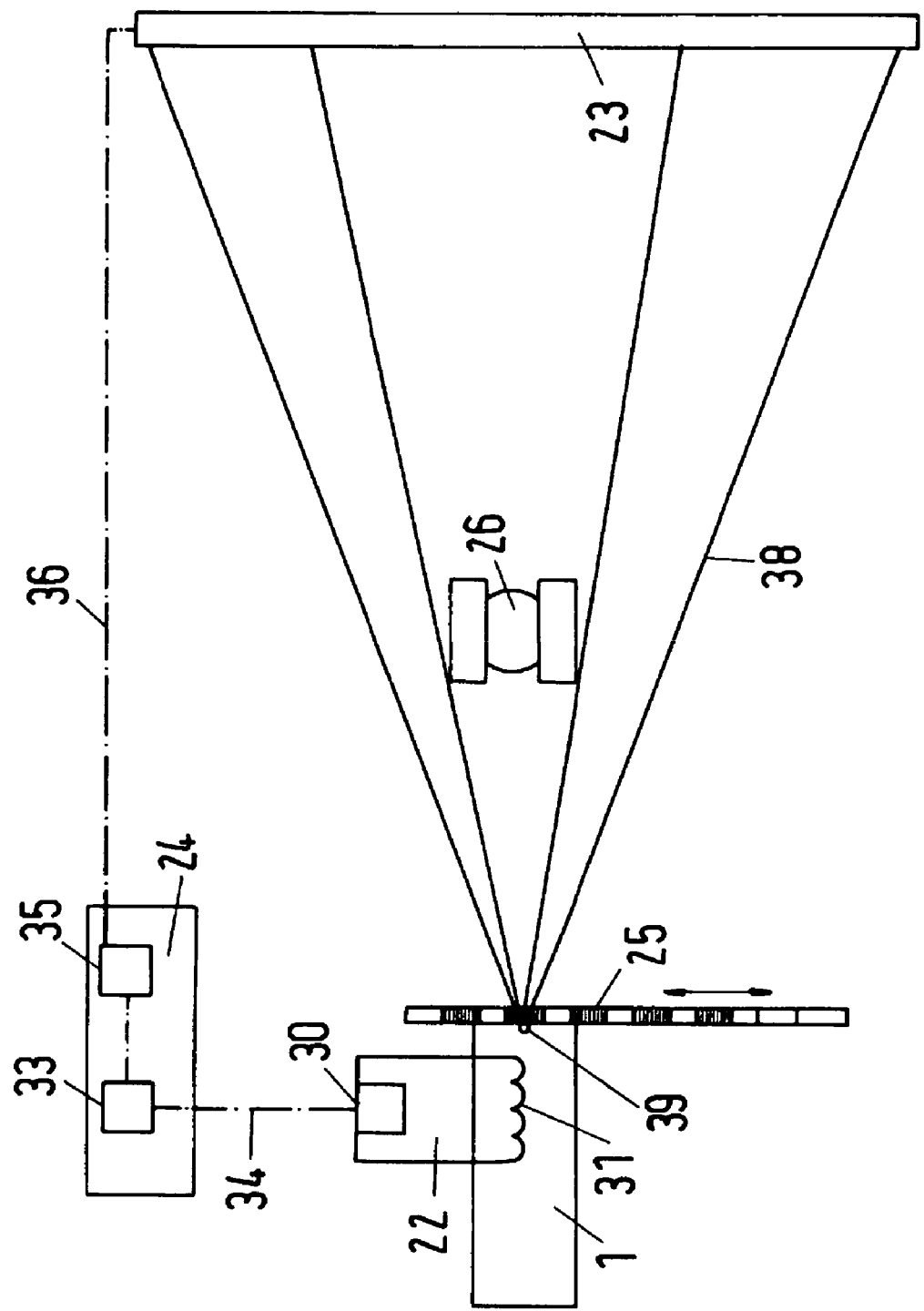

FIG. 2 shows a radiation producing device 1, e.g. the X-ray tube in accordance with FIG. 1. The radiation producing device 1 has an adjustable focusing device 22, which has e.g. at least one magnet coil 31. The coil current is adjusted by an actuating device 30, to be precise depending on an actuating signal received by the actuating device 30 from a control unit 33, which are connected to one another via a control signal line 34.

The control unit 33 is e.g. part of a computer 24, which additionally also has an evaluation device 35. The control unit 33 is connected to the evaluation device 35 and, in producing the control signals to be output to the actuating device 30, takes account of results of the evaluation of images that is carried out in the evaluation device 35.

The evaluation device receives information about the images via a connection 36 from an image producing device 23, which has detectors sensitive to X-ray radiation and is configured for producing a two-dimensional image corresponding to an X-ray radiation pattern incident on the image producing device 23. In this case, the individual detectors of the image producing device 23 can be configured such that they integrate the impinging X-ray radiation over time or detect the temporal profile. The integration or the temporal profile can also be performed or provided by a recording device (not illustrated) of the image producing device 23 for recording the image signals supplied by the detectors. The image producing device 23 can be configured as known per se from the prior art for CT examinations and can be in particular an image producing device for the examination of technically and/or industrially produced objects.

FIG. 2 additionally illustrates a diverging radiation bundle or the side view of a radiation cone 38 issuing from the focal spot 39 of the radiation producing device 1. Situated in the beam path of the X-ray radiation is a measurement object 26 which is intended to be examined and from which a three-dimensional image data record is produced e.g. after reconstruction from a plurality of images (radiographs recorded by means of the arrangement illustrated in FIG. 2 for different rotational positions of the object 26), the voxels (volume elements) of said image data record each having a grey-scale value corresponding to the extinction in the respective assigned volume element of the object 26.

At the radiation producing device 1, a movable mount 25 is arranged directly behind the exit opening or directly behind the exit cross section through which the electromagnetic radiation emerges from the device 1, said mount being fixed in particular to an outer wall and/or to a body of the radiation producing device 1. As indicated by the double-head arrow shown in FIG. 2, the mount 25 can be moved in a direction transversely with respect to the beam path, such that optionally specific structures and/or articles can be positioned in the beam path. By way of example, as is indicated by the sequence of dark and light regions of the mount 25, the articles and/or structures are arranged alongside one another and can thus be optionally introduced individually into the beam path by displacement of the mount 25 relative to the exit cross section.

As an alternative or in addition, a plurality of the structures and/or articles can be held by the mount in such a way that they can be simultaneously introduced into the beam path, in particular alongside one another and/or one behind another in the propagation direction of the radiation. The mount can also be rotatable, such that one or a plurality of the structures and/or articles can be introduced into the beam path by rotation.

The articles are, in particular, filters for filtering the radiation passing through. The structures are, in particular, one or a plurality of calibration objects. A particularly preferred embodiment of a calibration object with a plurality of structures will be discussed in more detail with reference to FIG. 5 to FIG. 8.

Figure 10:
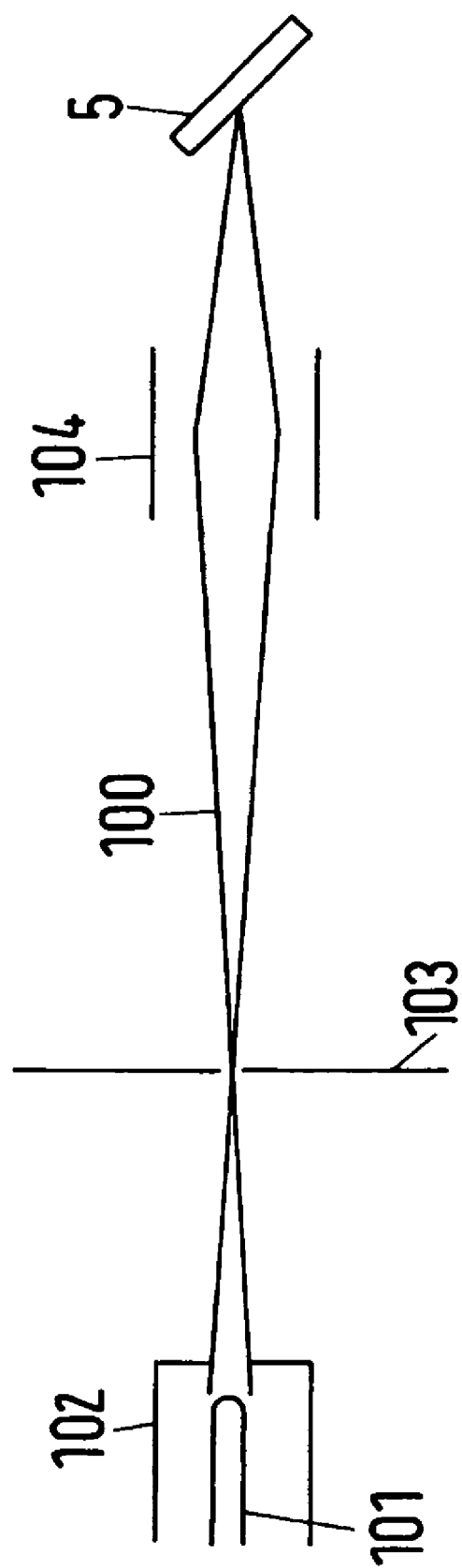
FIG. 10 shows an arrangement for accelerating and focusing electrons which is integrated e.g. into the X-ray tube in accordance with FIG. 1.

FIG. 10 shows a concrete exemplary embodiment of an arrangement for producing the particles (here electrons) and for focusing the partial beam onto a target. A heating filament 101, through which electric current flows, emits the electrons. The heating filament can have a single bend, for example, at which the electrons are emitted (so-called hairpin filament). The electrons are accelerated by the application of an electrical voltage between the heating filament 101 (cathode) and an aperture diaphragm 103 (anode) disposed downstream in the propagation direction of the electron beam. The corresponding usable part of the electron beam is designated by the reference symbol 100. Situated between the heating filament 101 and the aperture diaphragm 103 is a second aperture diaphragm 102, which is a Wehnelt cylinder, for example. The aperture diaphragm 103 acts as an electrostatic lens and prefocuses the electron beam. The usable part 100 of the electron beam thus has a constriction (crossover) in the plane of the aperture diaphragm (anode plane). In the further course of its propagation, the usable part 100 of the electron beam passes a focusing device 104, which is a magnet coil, for example. As an alternative, the focusing device 104 can also be configured differently and be e.g. a capacitor arrangement. Moreover, instead of a single focusing device 104, in the region of the radiation path of the electrons that is free of an electric field, that is to say in the region behind the anode, it is possible to provide a plurality of focusing devices lying one behind another in the radiation direction (that is to say on the path). As a result, the electron beam is always focused onto the focal spot in the target 5 if the focusing device or the focusing devices is or are adjusted correctly.

Figure 3:
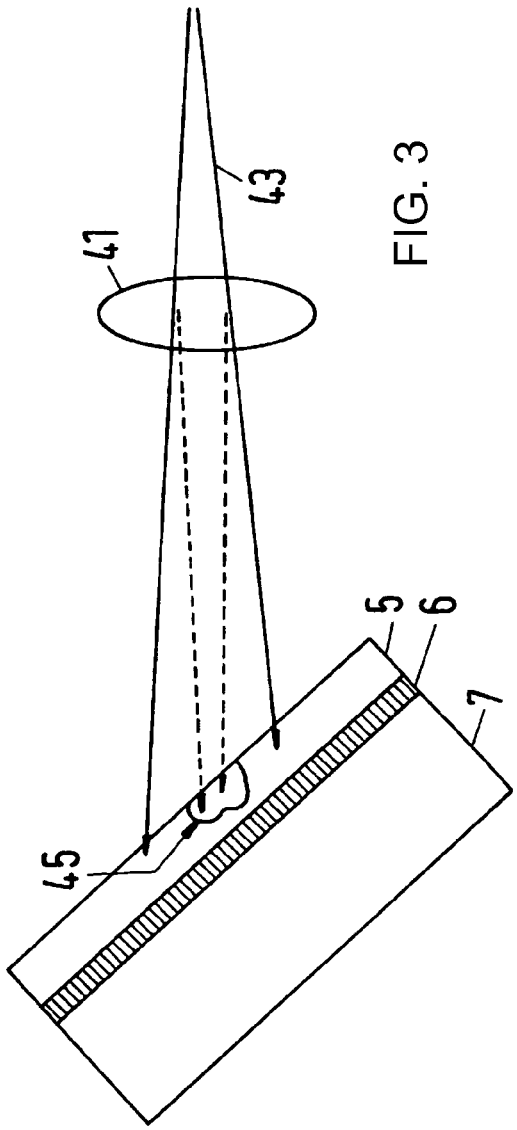

FIG. 3 shows an electron beam which, coming from a source from the right in the figure, passes through an adjustable magnetic field 41, produced e.g. by the focusing device 22 illustrated in FIG. 2. The electron beam 43 can thereby be focused onto a target 5, which is connected to a base 7 via a layer 6 of a connecting material (e.g. a hard solder).

FIG. 3 shows the effect of two different states of the magnetic field 41. In a first state, the electron beam 43 propagates in diverging fashion, as illustrated by the two solid arrow lines, through the magnetic field 41 until it impinges on the target 5. This is associated with a large dimensioning of the focal spot on the target 5 at which the electrons impinge on the material of the target 5. In a second state of the magnetic field 41, the diverging marginal rays of the electron beam 43, as illustrated by the dashed arrow lines in FIG. 3, are deflected and focused onto a significantly smaller focal spot 45 in the target 5. By fine adjustment of the coil current, the magnetic field 41 can be varied such that the size of the focal spot 45 (measured or considered along the surface of the target 5) reaches a specific predetermined value or reaches a value which produces a desired effect in a radiograph. By way of example, by adjusting the magnetic field 41 or varying the coil current, the size of the focal spot 45 is adjusted such that it is possible to find images of structures of a calibration object with a predetermined minimum resolution and/or with a maximum resolution in the radiograph.

Figure 4:
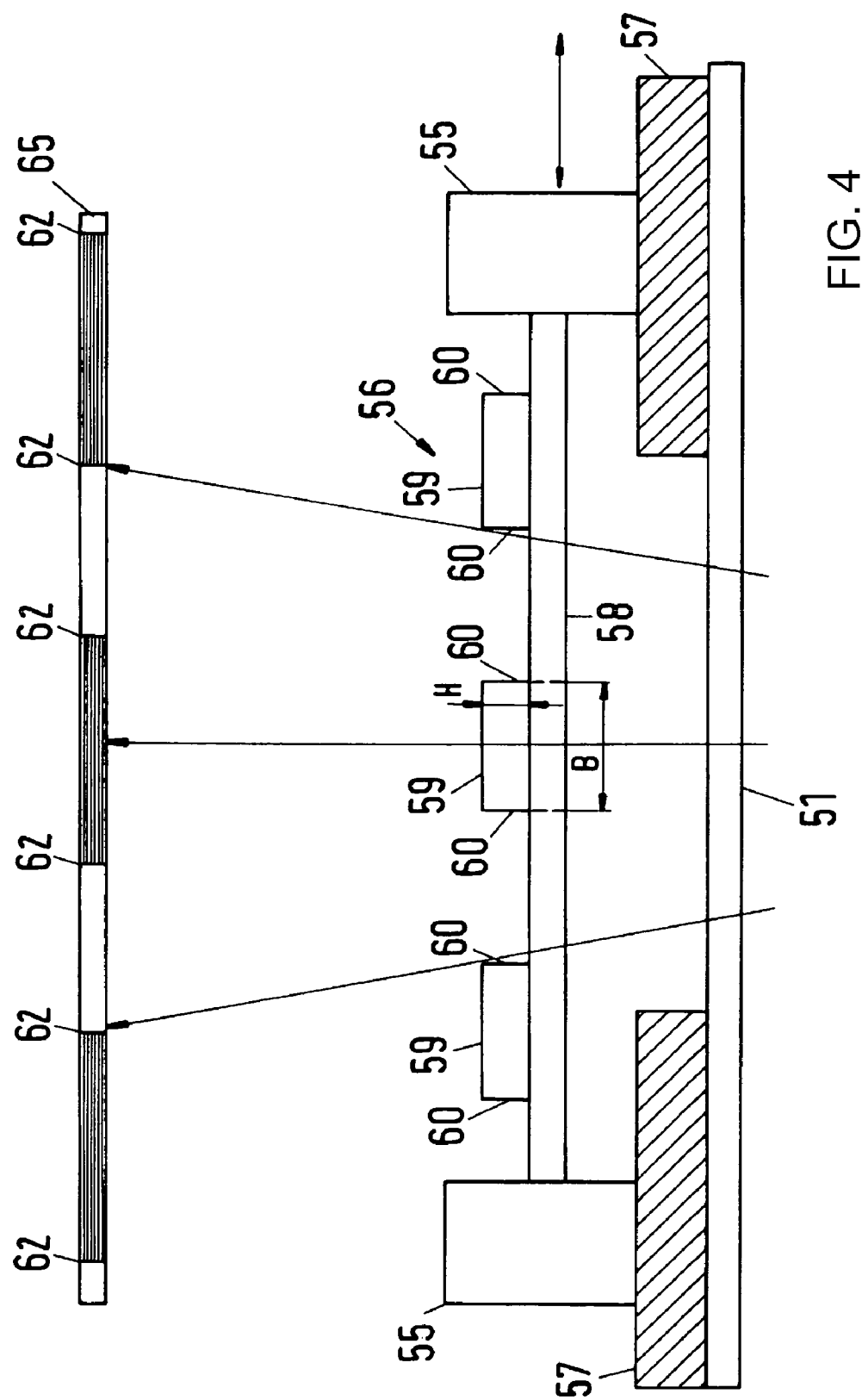
FIG. 4 shows a partial illustration of the arrangement illustrated in FIG. 2, illustrating the imaging of a calibration object onto an image producing device.

FIG. 4 shows an exit window 51 of the radiation producing device, through which the electromagnetic radiation, as indicated by three arrows, propagates to outside the radiation device. A mount 55 for a calibration object 56 is arranged directly in front of the exit window 51 in a manner displaceable transversely with respect to the radiation direction. In particular, a guide 57 for guiding the displacement movement of the mount 55 is directly or indirectly connected fixedly to the window 51. In this way, the mount 55 can be brought reproducibly to a specific relative position with respect to the window 51 and the target (not illustrated in FIG. 4). By way of example, the mount 55 can be configured such that it latches in the specific relative position. The guide 57 can moreover be configured such that it not only guides the movement of the mount 55 but also holds the latter. Therefore, the mount 55 cannot inadvertently become detached from the guide 57.

As already mentioned, the mount 55 holds a calibration object 56. Said calibration object 56 has a disc-shaped carrier 58 composed of a material (preferably glassy carbon) in which the electromagnetic radiation is only very slightly absorbed and/or scattered.

Regions 59 composed of a different material than the carrier layer 58 are formed at a surface of the carrier layer 58. Said material has a significantly higher attenuation coefficient (scattering and absorption) for the electromagnetic radiation. Gold, for example, is well suited to X-ray radiation.

The material regions 59 have edges 60 running approximately in the propagation direction of the electromagnetic radiation. Accordingly, radiation patterns 62 corresponding to the material regions 59 are produced on the image producing device 65, which can be configured like the image producing device 23 in accordance with FIG. 2.

In order to be able to obtain the sharpest possible edges or margins of the material regions 59 projected onto the image producing device 65, the material regions 59 have a highest possible aspect ratio (height H divided by distance or width B). Instead of the width B it is also possible to use the distance between the material regions 59 for the definition of the aspect ratio. In the schematic case illustrated in FIG. 4, the aspect ratio is approximately 1:3. In particular for high powers of the radiation producing device, however, an aspect ratio of at least 0.6, preferably more than 0.8, is proposed. A high power is understood to be a value of the electron beam power of a microfocus X-ray tube within the range of 100 W to a few 100 W (e.g. 320 W).

Figure 5:
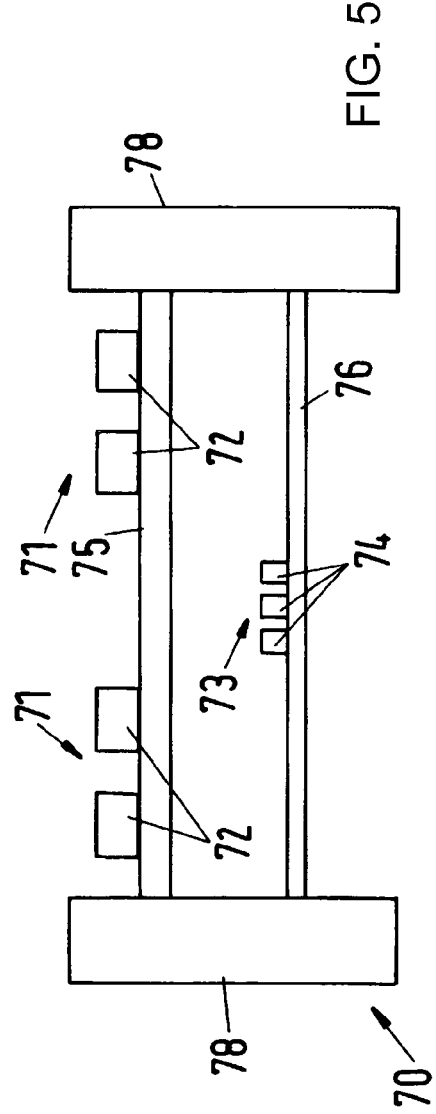
FIG. 5 shows a calibration object with two different partial structures having different scalings.

FIG. 5 shows a calibration object with two, differently scaled structures 71, 73. A mount 78 is in turn provided, which can be provided for example instead of the mount 55 in accordance with FIG. 4 or as part of the mount 25 in accordance with FIG. 2. In particular, a relative movement of the mount 78 relative to a radiation producing device can be possible, such that the structures 71, 73 can be introduced into the beam path of the electromagnetic radiation as necessary.

In the illustration in accordance with FIG. 5, the radiation would, from the bottom to the top, pass through the structures 71, 73 or pass said structures if the mount 78 has been positioned accordingly. In general, detached from this exemplary embodiment, it is preferred for the edges of the material regions in this case to be oriented parallel to the optical axis (e.g. by means of monolithic elements in the form of leaf-spring parallelograms). The radiation therefore firstly passes through a carrier layer 76 of the structure 73. In the material regions 74 forming the structure 73, a considerable attenuation of the electromagnetic radiation passing through then takes place. The attenuated radiation and the radiation which has passed the structure 73 at a close distance from the material regions 74 without attenuation passes through the structure 71 in the further beam path without attenuation in said structure.

On the other hand, radiation which has passed essentially without attenuation through the carrier layer 76 and which has passed the material regions 74 at a greater distance passes in partial regions firstly through a carrier layer 75 of the structure 71 and is then attenuated by attenuation in material regions 72 of the structure 71. Another portion of the radiation, which was likewise not attenuated by the material regions 74 of the structure 73, also passes the material regions 72 without significant attenuation. In this way, solid angle ranges for the propagation of the electromagnetic radiation in the direction of the image producing device exist in which an image of the structure 73 is produced, and other solid angle ranges exist in which an image of the structure 71 is produced. Therefore, structures of different types can be provided in the same calibration object, in particular in order to perform a calibration (by adjustment of the focusing device) in different power ranges of the electron beam or of some other particle beam. As can be discerned from FIG. 5, the height of the material regions 72 of the structure having the wider material regions is higher than in the structure having the narrower material regions 74. The illustration is a schematic illustration. In practise, it is preferred for the aspect ratio of the structure or structures having a larger width of the material regions and/or having larger distances between the material regions to be greater than in the structure having smaller dimensions transversely with respect to the beam path.

Figure 6:
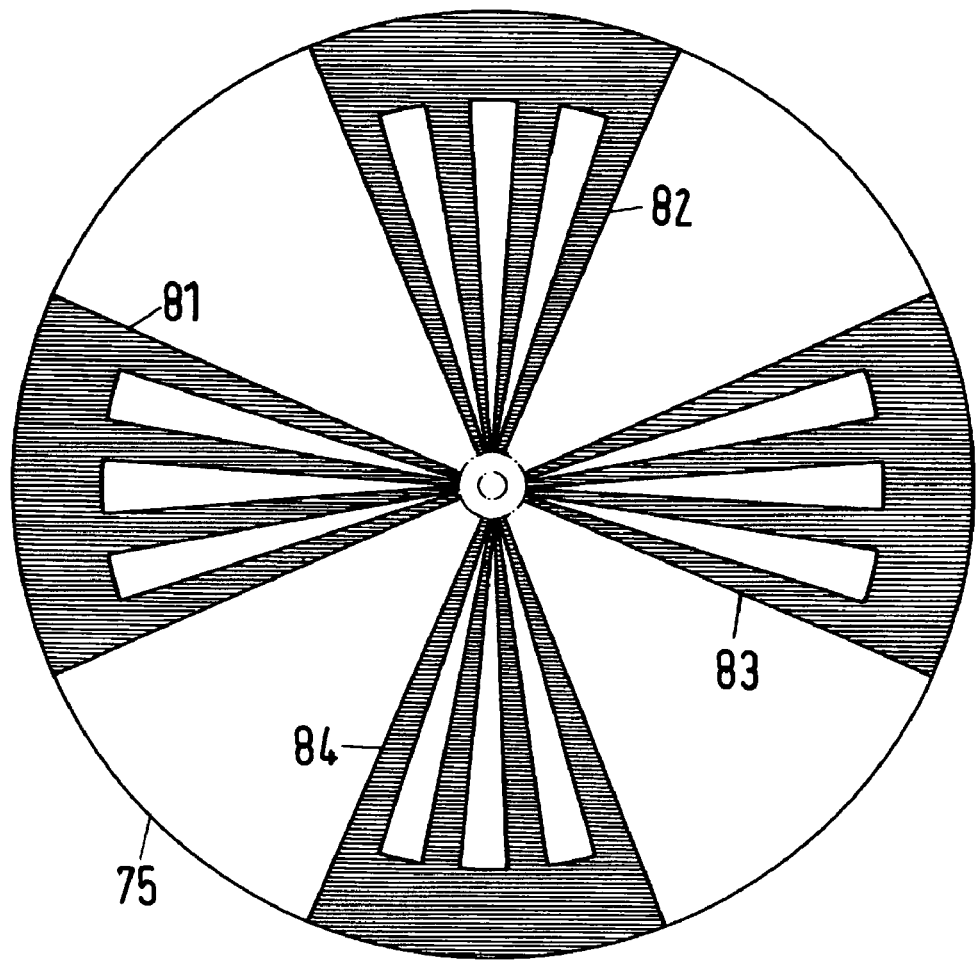
FIG. 6 shows a concrete embodiment of the partial structure illustrated schematically in FIG. 5 with larger dimensions.
Figure 7:
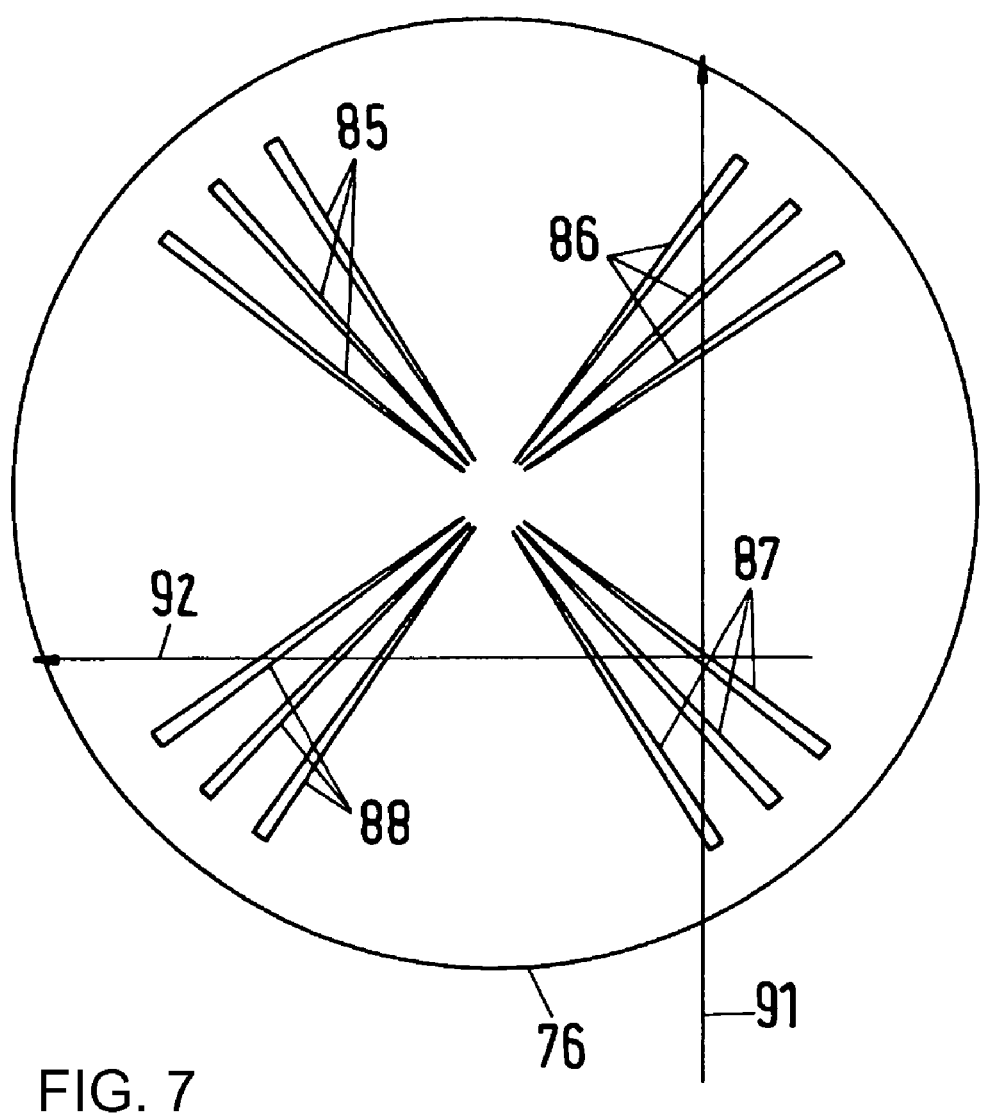
FIG. 7 shows an illustration of a concrete embodiment of the partial structure illustrated schematically in FIG. 5 with smaller dimensions.

FIG. 6 and FIG. 7 show the radiograph and the view of two different structures which can be arranged e.g. jointly in a calibration object of the type in accordance with FIG. 5 in the beam path or the radiographs of which can be recorded simultaneously by an image producing device. The two structures are arranged for example on the disc-shaped carriers 75 and 76 which are indicated by the circular line in FIG. 6 and FIG. 7, respectively, and which can be the carriers in accordance with FIG. 5. However, the material regions of the structure having the larger dimensions are configured (shaped and arranged) differently than the material regions 72 in accordance with FIG. 5.

FIG. 6 shows, represented by darker areas, the regions on the carrier 75 which are material regions of the material that is absorbent for the radiation. Therefore, there are a total of four circle segments present within which material regions 81 to 84 are actually situated which can lead to a significant attenuation of the electromagnetic radiation. Within these circle segments, however, three radial regions in each case are cut out, wherein these regions as well as the circle segments extend from the inner end outward in a radial direction relative to the midpoint of the carrier 75. In this case, the cut-out regions as well as the circle segments also become wider from the inner end outward. However, the cut-out regions can already end at a distance from the outer radius of the circle segments.

By contrast, in the structure in accordance with FIG. 7, only a plurality of material regions 85 to 88 composed of absorbent material are applied on the carrier 76, wherein these material regions have a form and relative arrangement with respect to one another like the cut-out regions of the structure in accordance with FIG. 6. However, the dimensions of the material regions 85 to 88 are smaller than the outer dimensions of the cut-out regions in accordance with FIG. 6. In particular, the through the angular distance (relative to the angular scale around the midpoint of the circular carrier 76), the outer edges of the material regions 85 to 88 is significantly smaller than the angular distance of the outer edges of the cut-out regions in accordance with FIG. 6. Preferably (unlike in the illustration in FIG. 7) the angular distance between the individual material regions 85, 86, 87, 88 is also smaller than the angular distance between the cut-out regions in accordance with FIG. 6. Therefore, both with regard to the width of the material regions and with regard to the distances between the material regions, the structure can have smaller dimensions than the structure in accordance with FIG. 6.

Figure 8:
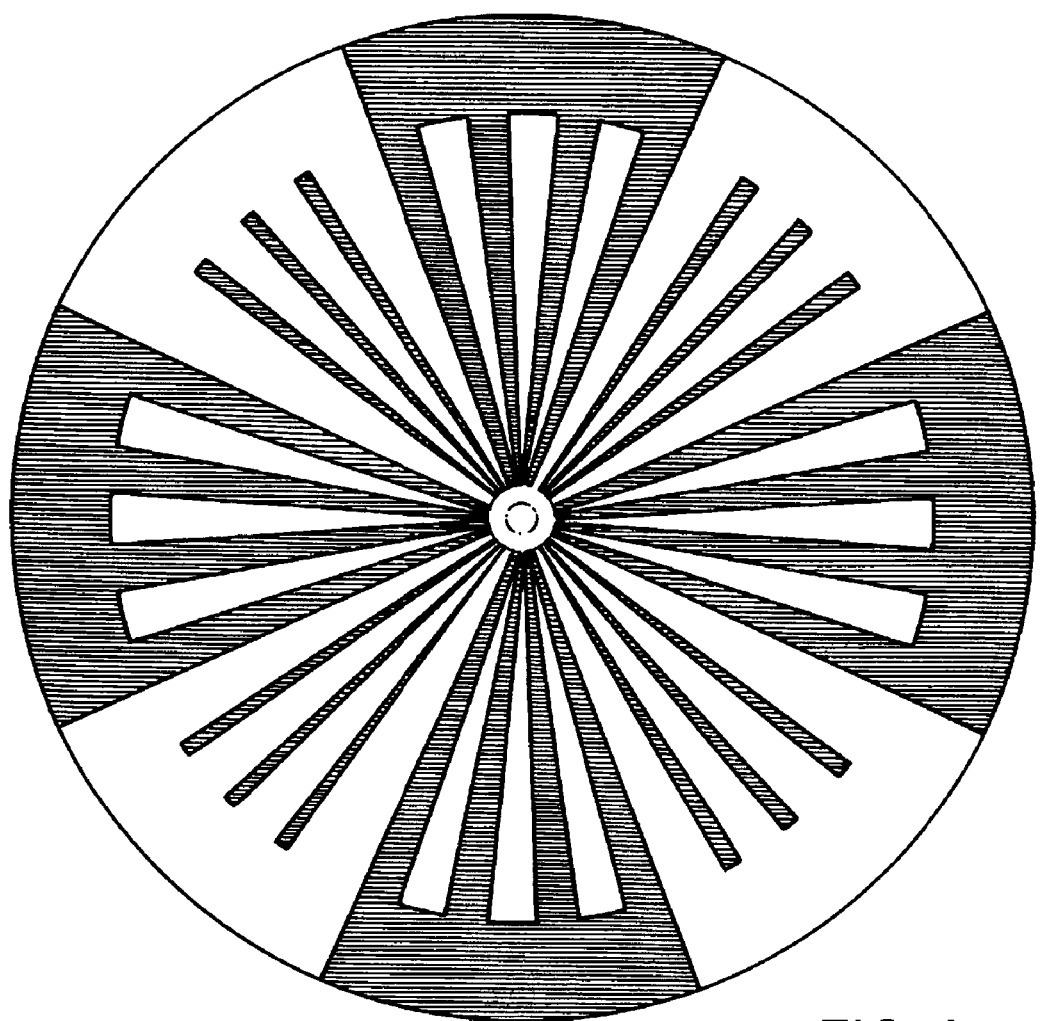
FIG. 8 shows a view showing how the partial structures in accordance with FIG. 6 and FIG. 7 are distributed over a solid angle range in which the electromagnetic radiation propagates.

The structures in accordance with FIG. 7 and FIG. 8 both have areas occupied by material. The absolute contrast ratio can be determined therefrom, which ratio is ideally 1 but is less than 1 in the exemplary embodiment on account of the finite thickness of the material and on account of the attenuation in the carrier material. The spatial resolution can be specified as MTF (Modulation Transfer Function). In particular, a transfer ratio can be specified for each structure width (specified as line pair per mm). A structure width (LP/mm) given an MTF of approximately 30% is generally specified as a characteristic value of the resolution (in detector technology). The total MTF can be documented as a quality feature of the arrangement for one or more given operating states.

Parameters of the operating state are, in particular, the power of the particle beam, the magnification and the adjusting value or values of the focusing device.

FIG. 8 shows the radiograph and the view of the two structures in accordance with FIG. 6 and FIG. 7 if they are arranged one behind the other in the manner of the calibration object in accordance with FIG. 5 in the beam path. It can be discerned that the structures having the smaller dimensions and the structures having the larger dimensions are imaged in each case in four solid angle ranges with a circle-segment-shaped cross section.

If, by way of example, the structure in accordance with FIG. 7 is evaluated in order to determine the image resolution and/or the contrast present in a radiograph, it is possible, as indicated in FIG. 7, to effect evaluation along the two arrow lines 91, 92 perpendicular to one another. In this case, the directions of the arrow lines 91 and 92 can correspond to the directions of the rows and columns of the individual detectors of the image producing device. Therefore, for example just one row and one column of the detectors need be evaluated. Moreover, the edges of the structures are preferably oriented such that the evaluation directions intersect the edges perpendicular to the course thereof. The evaluation lines cannot therefore also be significantly shorter than is illustrated in FIG. 7. The evaluation involves, in particular, the following procedure:

The sequence of detectors formed by the row or column supplies in each case an image value, for example a grey-scale value, which corresponds to the intensity of the impinging radiation. The difference between the image values is then determined for each pair of detectors succeeding one another in the sequence. In order that higher differences corresponding to higher contrasts and thus higher obtained resolutions are weighted higher, the differences are squared. This also eliminates the sign, which is unnecessary for the evaluation of the differences. The sum of the squares of the differences is formed and used as the result of the evaluation for the adjustment of the focusing device.

Figure 9:
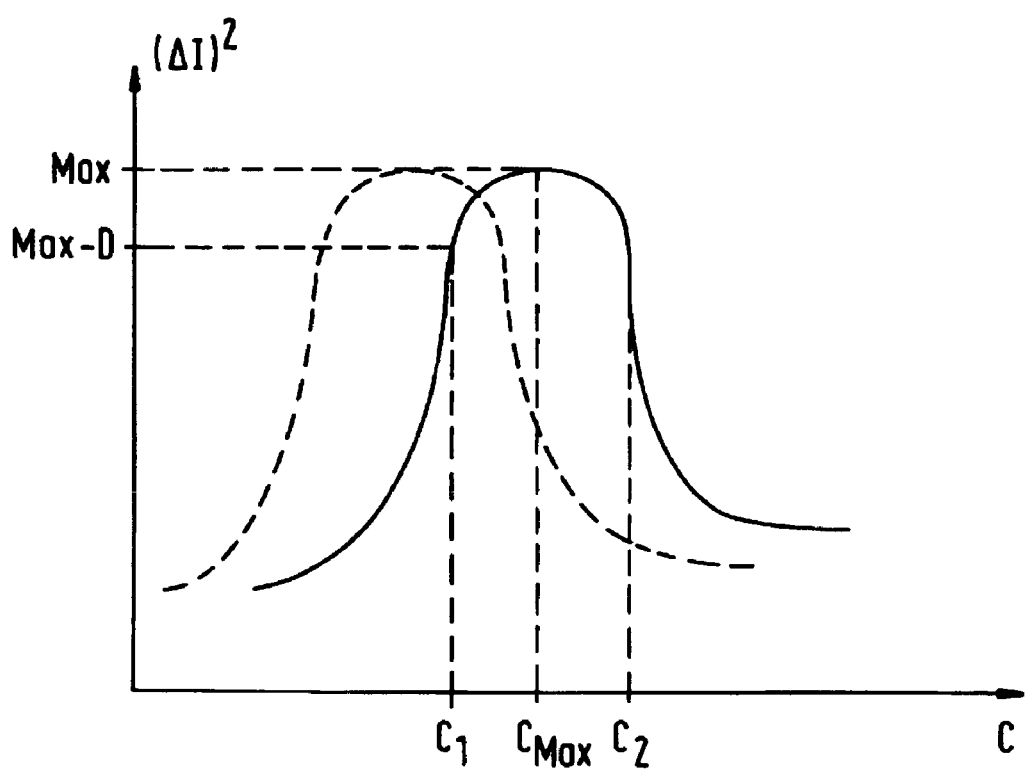
FIG. 9 shows the image resolution and the contrast of a radiograph as a function of the coil current of a focusing device.

FIG. 9 schematically shows the dependence of this result variable, which is symbolized by $(\Delta I)^2$, on the coil current C of the focusing device. It is evident starting from small values of the coil current C that the contrast rises significantly and is very high already at the value $C_1$. As the coil current C rises further, the maximum of the contrast is reached at $C_{Max}$.

As the coil current C rises further, the contrast decreases again greatly. The contrast typically lies in the range between "Max-D" and "Max" during continuous operation. In this case, the dependence of the contrast on the coil current C can shift in the manner indicated by a curve represented by a dashed line in FIG. 9. This may be caused by changes in the temperature both of the environment and of parts of the radiation producing device. However, other influencing factors, such as, for example, the electric current of the electron beam of an X-ray tube or the accelerating voltage of the electron beam, also lead to a different dependence between the contrast and the coil current C. Therefore, preferably repeatedly the calibration object is introduced into the beam path and the maximum of the contrast is adjusted again by altering the coil current. In this case, the maximum can lie at a different contrast value than before. Therefore, it is preferred to adjust different values of the coil current and to determine or find the maximum of the contrast using the contrasts resulting from the different coil currents. In this case, it is possible for example to form the derivative of the contrast with respect to the coil current.

As an alternative or in addition to the coil current, it is possible to adjust the current through an emission device for emitting the particles which impinge on the target at the focal spot and produce the electromagnetic radiation there. This is applicable to all the embodiments of the invention unless it is expressly mentioned that no adjustment of the emission device is performed as part of the adjustment of the focusing device.

In practice, focusing devices comprising a plurality of partial focusing devices which are adjusted in a multistage process also exist. In this case, e.g. a first step involves firstly adjusting the power of the electron beam and/or the current through the emission device (e.g. heating filament) and performing a corresponding pre-adjustment of the focusing device or of other parts of the focusing device. Afterward, e.g. a second step involves adjusting, in the manner according to the invention, a first one of two focusing devices that succeed one another in the electron radiation direction. Afterward in turn e.g. a third step involves adjusting, in the manner according to the invention, the second one of the two focusing devices that succeed one another in the electron beam direction. In particular the second and third steps can also be performed repeatedly, such that the focusing is effected in an iterative method.

In the case of particularly small dimensions of the focal spot and in the case of high electron beam powers, an overheating of the target material can occur, it is possible, therefore, that a minimum value of the focal spot dimensioning has to be adjusted which does not correspond to the maximum contrast that can be achieved. Therefore, e.g. an upper limit for the contrast can also be predetermined, which must not be exceeded. In this case, adjustment is effected not to the maximum contrast but rather to the upper limit value. It is also possible, in the manner according to the invention, to adjust the spatial resolution in the radiograph or voxel size in a CT volume data record by evaluation of one or a plurality of radiographs. This is preferably done before the first recording that is recorded for the examination of a measurement object.

This is a crucial advantage particularly for the reconstruction in the case of computer tomography (CT), since it is possible to avoid carrying out (computing) the reconstruction with smaller voxel sizes than is expedient for an adjusted contrast in the radiographs.

The calibration object in accordance with FIG. 7 to FIG. 9 has the advantage that it is possible to evaluate both the structure having the smaller dimensions and the structure having the larger dimensions transversely with respect to the direction of the electromagnetic radiation for smaller or larger radii with respect to the center of the structures. As a result, for different operating situations of the arrangement, the suitable regions of the structure can be evaluated in each case without having to replace the calibration object. By way of example, in the case of very small electron beam powers of less than 10 W, the structure in accordance with FIG. 7 is evaluated near the center. The smallest distances and smallest widths of the material regions are encountered here.

By contrast, in the case of very high electron beam powers and in particular also in the case of high accelerating voltages of the electron beam of the X-ray tube, evaluation is effected in the radially outer region of the structure in accordance with FIG. 6. The largest widths and largest distances of the cut-out regions are encountered here. In order in this case still to obtain attenuation of the electromagnetic radiation in the material regions that suffices for an evaluation, said material regions are intended to have a large height, in particular a height of more than 0.2 mm, preferably more than 0.5 mm, for an accelerating voltage of more than 200 kV.

Instead of the contrast, it is also possible to use the spatial resolution as the result of the evaluation of the radiograph or radiographs for the adjustment of the focusing device. This involves determining, for example, how many line pairs of adjacent edges of the material regions can be determined per millimeter of evaluation distance (which runs transversely with respect to the course of the edges). In this case, it is possible to predetermine a criterion of what difference between adjacent pixel or what value of the gradient of the image values in the direction of the evaluation distance can still be regarded as an indication of the presence of an edge or line.

By arranging a plurality of filters which are retained by the mount and are introduced into the beam path optionally or at the same time, it is possible to vary the attenuation in the filter material. As an alternative or in addition, it is possible to introduce optionally just one of a plurality of filter materials or different filter materials simultaneously into the beam path. A large variation in the filter results is possible in this way.

The entire mount can also have a plurality of movable parts which in each case retain one or a plurality of filters and/or a calibration object. In particular the abovementioned combinations of different or identical filters in the beam path can be obtained in this way. Moreover, it is possible to position the calibration object together with one or more filters in the beam path, in order e.g. to simulate realistic measurement conditions.

In particular, the mount or at least one of the movable parts of the mount has a window-like configuration, wherein the filter or the calibration object is arranged in the window opening. A window-like configuration has the advantage that a circumferential frame is formed, such that the filter or the calibration object can be retained in a mechanically stable manner. In particular, the filter or the calibration object is clamped in between two parts of the window frame and thus retained, wherein the two parts of the window frame lie one behind the other along the propagation direction for the electromagnetic radiation. In this way, a self-contained circumferential margin of the filter of the calibration object can be clamped in. For clamping in, the frame parts can be screwed to one another, for example, wherein the longitudinal axis of the screws also extend parallel or approximately parallel to the beam path of the electromagnetic radiation.

The invention claimed is:

1. A method of operating a configuration for producing electro-magnetic radiation, which comprises:
    directing particles onto a target by way of an adjustable focusing device, for producing electromagnetic radiation in the target;
    placing a measurement object in a beam path of the electromagnetic radiation, and radiating the electromagnetic radiation through a measurement object;
    providing a calibration object and movable mount for moving the calibration object;

for adjusting the focusing device, temporarily introducing the calibration object into a predetermined position relative to the target and in the beam path of the electromagnetic radiation by way of the movable mount, in addition to the measurement object and without removing the measurement object from the beam path, recording a radiograph of the object or recording a plurality of radiographs and subsequently removing the calibration object from the beam path by actuation of the mount;

automatically evaluating the radiograph or the plurality of radiographs; and adjusting the focusing device in dependence on the evaluation obtained in the evaluating step.

2. The method according to claim 1, which comprises directing electrons onto the target.

3. The method according to claim 1, which comprises generating in the target X-ray radiation or extreme ultraviolet radiation.

4. The method according to claim 1, which comprises adjusting the focusing device depending on the evaluating step to drive at least one of a spatial resolution obtained in a resulting radiograph and an image contrast of the resulting radiograph to a predetermined value.

5. The method according to claim 1, which comprises adjusting the focusing device depending on the evaluating step to drive at least one of a spatial resolution obtained in a resulting radiograph and an image contrast of the resulting radiograph to a maximum.

6. The method according to claim 1, which comprises introducing one or a plurality of filters for filtering the radiation and/or the calibration object into the beam path of the electromagnetic radiation by actuation of the mount.

7. The method according to claim 6, which comprises evaluating grey-scale values in the respective image along a line running transversely with respect to an edge profile produced by the edges.

8. The method according to claim 6, which comprises evaluating the change in the image values along two different lines running transversely with respect to one another in the respective image.

9. The method according to claim 1, which comprises placing the calibration object nearer to the target than the measurement object.

10. The method according to claim 9, which comprises placing the calibration object at a radiation producing device having the target.

11. The method according to claim 1, which comprises providing the calibration object with structures formed by edges of a material region or by edges and/or margins of a plurality of material regions, and wherein the step of evaluating the at least one radiograph comprises evaluating a change in image values in the respective image along a line running transversely with respect to an edge profile produced by the edges, and adjusting the focusing device in dependence on the change.

12. A configuration for producing electromagnetic radiation, comprising:
an adjustable focusing device configured for directing particles onto a target, for producing with the particles electromagnetic radiation in the target;
an image recording device for recording radiographs of objects through which the electromagnetic radiation radiates;
a movable mount and a calibration object held by said mount, said mount being movable for introducing said calibration object into a predetermined position relative to said target into a beam path of said electromagnetic radiation, and for removing said calibration object from the beam path by actuation of said mount and for returning said calibration object to the predetermined position;
an evaluation device connected to said image recording device and configured for automatically evaluating the radiograph or a plurality of radiographs, with the radiograph or radiographs showing a measurement object and said calibration object; and
an adjusting device connected to said evaluation device and configured to adjust said focusing device in dependence on a result of an evaluation by said evaluation device.

13. The configuration according to claim 12, wherein said particles are electrons.

14. The configuration according to claim 12, configured to produce X-ray radiation or extreme ultraviolet radiation.

15. The configuration according to claim 12, wherein said adjusting device is configured for adjusting said focusing device in dependence on an evaluation to drive at least one of a spatial resolution obtained in a resulting radiograph and an image contrast of the resulting radiograph to a predetermined value and/or to a maximum.

16. The configuration according to claim 12, wherein said mount additionally includes one or a plurality of filters for filtering the radiation and wherein said mount is configured to enable optional introduction of any of said filters and/or said calibration object into the beam path of the electromagnetic radiation by actuation of said mount.

17. The configuration according to claim 12, wherein said calibration object has structures formed by edges of a material region or by edges and/or margins of a plurality of material regions.

18. The configuration according to claim 17, wherein said structures have a first partial structure and a second partial structure, and wherein said edges and/or margins of said first partial structure are spaced at spacing distances greater than spacing distances in said second partial structure.

19. The configuration according to claim 18, wherein said edges and/or margins of said first partial structure and of said second partial structure extend in mutually different solid angle ranges relative to a propagation space of the electromagnetic radiation, to enable a radiograph of the first partial structure and of the second partial structure to be recorded simultaneously.

20. The configuration according to claim 17, wherein said edges and/or margins of said structures extend transversely with respect to the propagation direction of the electromagnetic radiation and approximately in a direction radially outward from an optical axis of the radiation.

21. The configuration according to claim 18, wherein said second partial structure is disposed closer to the target than said first partial structure in the beam path of the electromagnetic radiation.

22. The configuration according to claim 17, wherein said material region or said material regions forming said edges and/or margins are disposed on a carrier material that is transparent to the electromagnetic radiation.

23. The configuration according to claim 22, wherein said carrier material is composed of glassy carbon.

* * * * *